United States Patent [19]
Payton

[11] 4,175,028
[45] Nov. 20, 1979

[54] ELECTRODE MEMBRANE
[75] Inventor: Alan J. Payton, Harvard, Mass.
[73] Assignee: Corning Glass Works, Corning, N.Y.
[21] Appl. No.: 1,413
[22] Filed: Jan. 8, 1979
[51] Int. Cl.² .................... G01N 27/46; C25B 13/02
[52] U.S. Cl. ........................... 204/296; 204/195 P; 204/279
[58] Field of Search ............. 204/195 P, 1 P, 279, 204/295, 296; 324/29

[56] References Cited
U.S. PATENT DOCUMENTS

| 3,445,369 | 5/1969 | Porter et al. | 204/195 P |
| 3,577,332 | 5/1971 | Porter et al. | 204/195 P |
| 3,835,014 | 9/1974 | Huffhines | 204/195 P |

Primary Examiner—G. L. Kaplan
Attorney, Agent, or Firm—John P. DeLuca

[57] ABSTRACT

An electrode membrane structure comprising: an annular support member and a circular membrane portion integrally molded into said annular support, said membrane support being formed of sufficiently thin gas diffusible material, at least in the circular membrane portion and having an array of perforations to facilitate removal or separation of the annular support from the membrane portion, said support and membrane portions including an intermediate annular transition zone therebetween wherein the membrane portion increases in thickness to the support such that the gas diffusible material may be molded to the sufficient thinness required for gas diffusibility and yet maintain stability of dimension.

5 Claims, 5 Drawing Figures

ELECTRODE MEMBRANE

BACKGROUND OF THE INVENTION

This invention relates to an electrode membrane particularly adapted for use with a gas analysis electrode. Membranes of the type described herein are useful for providing a hydrophobic barrier over an end of a gas electrode, which barrier allows certain gases to penetrate into the electrode and yet blocks the passage of certain liquids therethrough.

In the past such membranes have been formed in sheets of a selected thickness sufficient to allow gas diffusion, with such sheets sandwiched between paper strips or secured to cardboard support members having through openings therein such that a window of the membrane material remained visible.

In practice, the membranes are generally disposed over an opening in the electrode and held in place with an appropriate retaining member such as an O ring, and after such mounting, the paper support is torn or cut away. The electrode is then utilized in an instrument such as a Corning Model 165 or 175 blood gas analyzer. The membrane material is a consumable item and must be changed at various required intervals.

The present invention provides a simplified membrane structure which may be compression-molded into an integral structure thus providing reduced cost and complexity of manufacture. In certain known devices a protective layer of paper is disposed over one side of the membrane and the entire structure may include an array of perforations for assisting in the removal of the paper support ring after use. Other devices contain no such protective layers or perforations and while they are consequently somewhat easier to manufacture, they have a tendency to be more difficult to use.

It has been found that there is a certain difficulty in molding an item of the type described herein since the membrane portion must be of a sufficient thinness to allow gas diffusibility and yet must be molded into a support portion capable of maintaining the membrane portion sufficiently stable of dimension. Thus when the membrane is stretched across the electrode opening, the support portion maintains its dimensional stability and strength and yet allows the membrane to be deformed across said electrode. As mentioned previously, such known support structures have been formed of a paper or cardboard structure with the attendant difficulty of fabrication. In the present invention, a compression mold has been developed which has a profile complimenting that of the article retained therein. The material could thus be molded or formed to a sufficient thinness in an operative region, with a transition zone between the membrane and the support member so that the desired results of practical molding could be achieved. That is, the material forming the membrane structure could flow from the membrane portion to the support member region via the transition zone.

SUMMARY OF THE INVENTION

There has been provided an electrode membrane comprising an annular support and a circular membrane portion integrally molded into said annular support, said membrane support being formed of a sufficiently thin gas diffusible material at least in the circular membrane portion, and having an array of perforations to facilitate removal or separation of the annular support from the membrane portion, said support membrane portion including an intermediate annular transition zone therebetween wherein the membrane portion increases in thickness to the support such that the gas diffusible material may be molded to the sufficient thinness required and yet maintain stability of dimension.

DESCRIPTION OF THE PREFERRED EMBODIMENTS

Figure 1A:
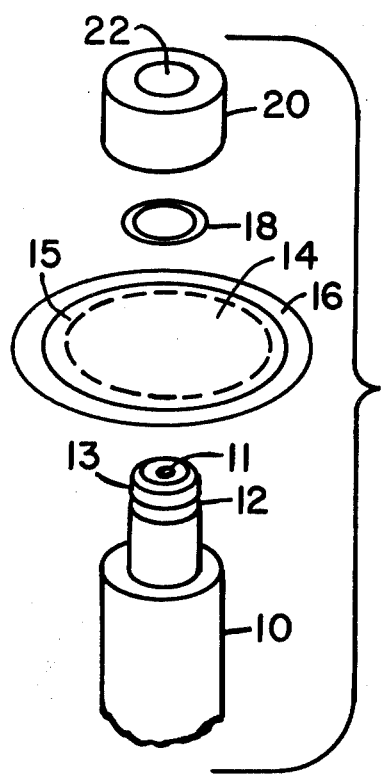
FIGS. 1a and 1b are respective successive exploded views of the mounting of a membrane on a gas diffusion electrode and showing an array of elements necessary to so mount a membrane thereon.
Figure 1B:
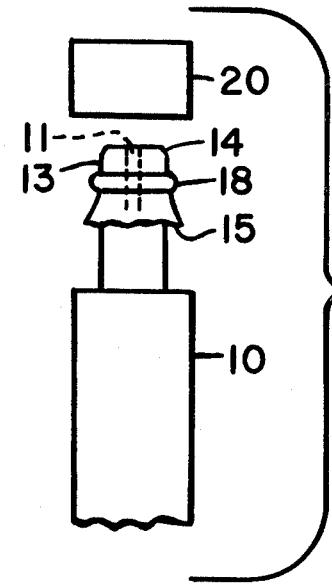

In FIGS. 1a and 1b there is shown successive exploded views of a number of elements necessary for implementation of gas diffusion analysis using a gas diffusion electrode 10. The electrode 10 has an opening 11 in a front portion of free end 13 thereof and has an annular recess 12 axially formed in the body of the electrode 10. A membrane 14, initially retained in a membrane support 16, may be disposed directly above the opening 11, and an O ring 18 is utilized to secure the membrane 14 in the annular recess 12. Boot 20 is used to protect the structure after the membrane is in place.

In FIG. 1b the next set of successive steps are illustrated wherein the membrane 14 has been stretched over the opening 11 in the electrode 10 and the O ring 18 has been force fit over the free end 13 of the electrode, and the membrane support 16 has been torn or cut away along perforations or tear line 15. The boot 20 is thereafter located over the free end of the electrode by means of an opening 22 which is axial with the opening 11 in the electrode 10. Thereafter the electrode 10 is immersed in a fluid for the detection of gas constituents therein. Remaining portions of the electrode or the instrument are not shown since they are not relevant to the invention other than the environment in which it is operating.

Figure 2:
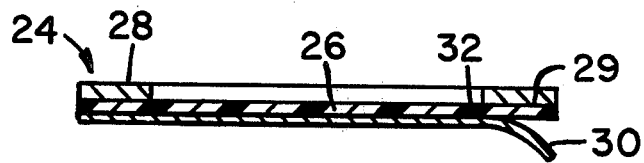
FIG. 2 is a cross-sectional schematic view of a prior art device utilizing a film of gas diffusible material supported on a paper annular member.

FIG. 2 illustrates a prior art membrane structure 24 wherein a membrane film 26 is stretched and retained in place by one paper or cardboard annular support ring 28. The ring 28 may be glued or fastened to the film 26 at an interface 29 therebetween. A protective layer of paper or other material 30 may be layered over one face of the film 26 and perforations 32 may be formed annularly around the film 26 near the inner edge of ring 28.

Figure 3:
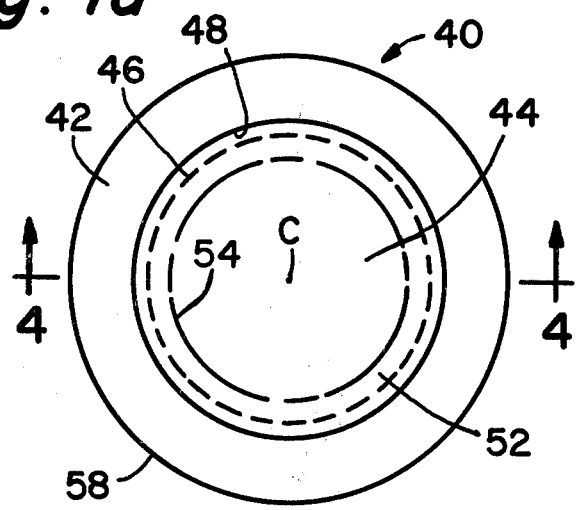
FIG. 3 is a top plan view of the electrode membrane structure of the present invention.

FIG. 3 illustrates the structure of the present invention wherein a membrane support structure 40 is provided which is integrally molded and includes an annular support portion 42 an annular transition zone 52, and a circular membrane portion 44 concentrically molded with each other. A circular array of perforations 46 is formed in the transition zone 52 and provides for easier removal or tearing away of the membrane portion 44 when it is utilized as described in FIG. 1b. The perforations are preferably located concentrically in transition 52 with a diameter of about 0.984", each perforation being about 0.22" long and spaced 0.05" apart. The structure is illustrated in side cross section in FIG. 4 wherein further details may be examined.

The membrane portion 44 extends from a center line C radially to a peripheral boundary 54 with transition zone 52, (see brackets 50), and is of a sufficient thickness t to allow for gas diffusion therethrough as indicated by the arrow 53. The membrane portion 44 dimensionally represented by brackets 50 is about 0.82" to 0.86". Dimension t of the membrane portion is between about 0.003" and 0.005". Annular transition zone 52 is disposed concentrically about membrane portion 44 and has a length of about 0.12". It extends radially outwardly to a peripheral boundary 48 of support portion 42 and has a curved inner surface 39 with a radius of curvature of about 0.03" (see brackets 56). The transition zone 52 begins near peripheral boundary 54 with a thickness t' increase from that of membrane portion 44 to a thickness t' about 0.010" to 0.012" near an inner radial end 38 of curved portion 39. The brackets 56 represent a dimension of about 0.12" for the transition zone 52. The annular support portion 42 is a relatively thick member having a thickness dimension T of about 0.5" to about 0.6". It extends radially outwardly from peripheral boundary 48 with transition zone 52 to an outer peripheral boundary 58 of the support structure 40 (see brackets 59). Its dimension is about 0.48" to about 0.52" as similarly represented dimensionally by the brackets 59. It should be noted that the transition zone 52 tapers in thickness from the dimension t at peripheral boundary 54 with membrane portion 44 to the larger dimension T at peripheral boundary 48 with the support portion 42, and thus allows for fine molding of the material of the support structure 40 to a sufficient thinness across the membrane portion 44, to allow for gas diffusibility thereof, and yet still provide the support function and semirigidity of the support member 42.

It should be noted that a mold, not shown, but which generally conforms to the profile of the membrane support structure 40 herein, is formed with a profile and dimensions complimenting that of the structure 40 such that the material used in forming it easily flows radially from the membrane portion 44 to the annular support region 42 through the transition zone 52. The tapered shape of the transition zone 52 facilitates this flow and provides the rigidity and structural integrity necessary to maintain dimension stability. Other dimensions than those mentioned above may be used if desired.

Some materials which are useful in the formation of the membrane structure herein are General Electric silicone rubber designated as SE-4524U, SE4404U, and SE4550U. Other products which might be also useful is Dow Corning silicone formulation S2000U and certain equivalents designated by that company. When these substances are aged over a period of days or weeks before molding they tend to produce membrane structures 40 having surfaces which form few or no droplets.

Figure 4:
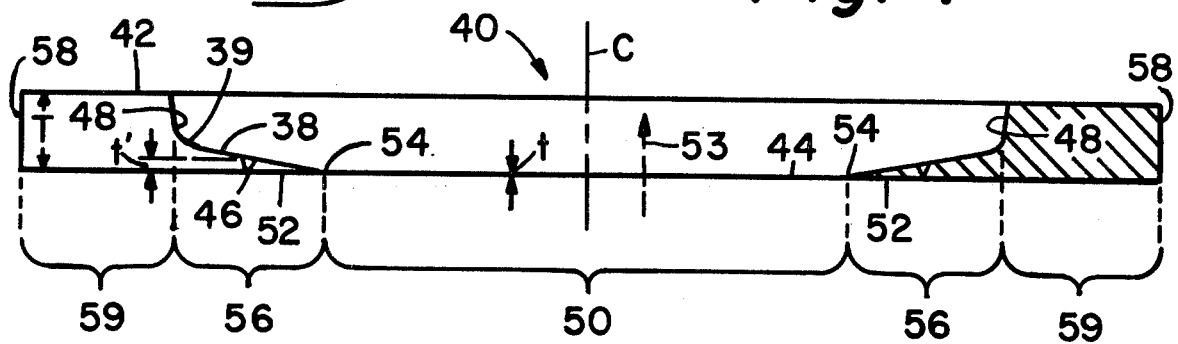
FIG. 4 is an enlarged cross-sectional elevational view of the electrode membrane structure of FIG. 3 taken along line 4—4 thereof.

It should be noted that there is ring of perforations which is illustrated at 46 in both FIGS. 3 and 4. Such perforations facilitate the removal of the annular portion 42 from the membrane portion 44. Membranes of the type described herein are generally strong, and if there are no through perforations therein they tend to maintain their strength by virtue of the film integrity. However if a perforation is provided through the material, a tear will ensue rapidly and with very little force. Thus the perforations 46 in the present invention have been provided, which do not necessarily pierce the film 44, but provide a very thin wall in the vicinity of the transition zone 52. Thus the membrane support structure 40 may be manually handled and subjected to considerable forces during the operation of forming the membrane over the electrode 10 as in FIG. 1b and yet tear away rather easily if one or more of the perforations 46 are started by some sharp implement.

While there has been described what at present is considered to be the preferred embodiment of the present invention, it will be obvious to those skilled in the art that various changes and modifications may be made therein without departing from the invention, and it is thus appended in the appended claims to cover all such changes and modifications as may fall within the true spirit and scope of the invention.

What is claimed is:

1. An electrode membrane structure comprising: an annular membrane support having a central membrane portion integrally molded with said annular support, said membrane structure being formed of a material which is gas diffusible when formed sufficiently thin to provide the central membrane portion, an array of perforations formed about the periphery of said central membrane portion to facilitate removal or separation of the annular support from the membrane portion, and an intermediate annular transition zone between said support and membrane portions wherein the thin membrane portion increases in thickness to that of the support, such that the gas diffusible material may be molded to the sufficient thinness required for diffusibility and yet maintain stability and dimension.

2. The electrode membrane structure of claim 1 wherein the membrane portion is centrally located in a circular portion and has a thickness of about 0.003 to about 0.0050".

3. The electrode membrane structure of claim 1 wherein said transition zone includes an axial tapered portion and a continuous smoothly curved portion extending from the membrane portion to the annular support, said tapered and smoothly curved portions providing for structural integrity and dimensional stability.

4. The electrode membrane structure of claim 1 wherein said array of perforations are located in the form of a circle therein, which perforations are formed as thin wall recesses in said transition zone.

5. The electrode membrane structure of claim 1 wherein the structure is integrally molded from a silicone rubber material which may be substantially deformed in said membrane portion and yet remain semirigid in said annular support.

* * * * *